United States Patent [19]

Yoshinaka et al.

[11] Patent Number: 4,507,510

[45] Date of Patent: Mar. 26, 1985

[54] PROCESS FOR PRODUCING XYLYLENEGLYCOL

[75] Inventors: Shigeo Yoshinaka; Tsukasa Toki; Tomoji Tsuji; Seiji Uchiyama, all of Niigata, Japan

[73] Assignee: Mitsubishi Gas Chemical Company, Inc., Tokyo, Japan

[21] Appl. No.: 566,377

[22] Filed: Dec. 28, 1983

[30] Foreign Application Priority Data

Mar. 7, 1983 [JP] Japan .................................. 58-36810

[51] Int. Cl.$^3$ ............................................. C07C 33/26
[52] U.S. Cl. ...................................... 568/811; 568/814
[58] Field of Search ................................. 568/811, 814

[56] References Cited

U.S. PATENT DOCUMENTS 2,967,854  1/1961  Bungs .................................. 568/811
3,422,143  1/1969  Bottomley ........................... 568/811

Primary Examiner—Werren B. Lone
Attorney, Agent, or Firm—Armstrong, Nikaido, Marmelstein & Kubovcik

[57] ABSTRACT

Xylyleneglycol is produced by diazotization reaction of xylylenediamine in the presence of more than 5 parts by weight of water per 1 part of xylylenediamine, while maintaining the PH of the reaction mixture in the range of 1.5 to 5.0.

15 Claims, No Drawings

PROCESS FOR PRODUCING XYLYLENEGLYCOL

BACKGROUND OF THE INVENTION

This invention relates to the process for producing xylyleneglycol by reacting xylylenediamine with nitrite.

Xylyleneglycol has the different characteristic from aliphatic glycol as the modifier or the raw materials of polyurethane or polyester resin and is recognized as an important material.

As the producing method of xylyleneglycol, the following methods are known so far.

(1) The process for producing xylyleneglycol by hydrolizing xylene dichloride directly in the presence of alkaline compound or by converting xylylenedichlolide into diacetoxymethylbenzene and hydrolizing the resulting diacetoxymethylbenzene.

(2) The process for producing xylyleneglycol by reducing aromatic dicarboxylic acid ester by hydrogen in the presence of a catalyst.

The first method has the defects, such as it requires a pressure vessel, requires a long reaction time and the process is long and complicated. In addition, it also has the essential defects, that is, the xylylenedichloride which is the raw material of the first method is produced by chlorination of xylene in general, but in that case, each of the two methyl groups which substitute aromatic nucleus cannot be monochlorinated selectively. And as the result, not only multichlorination of the methyl groups or chlorination of aromatic nucleus occurs simultaneously, useless chlorides are by-produced and the yield of objective product is decreased, but also the separation and purification of the reaction product are not easy (Japanese Patent Publication No. 54491/1982).

The second method is disclosed in Japanese patent publication No. 22814/1972, which method requires a pressure vessel and as the conversion rate of the reaction should be suppressed to prevent side-reaction, objective xylyleneglycol is obtained as the mixture with raw material and intermediate product. This requires separation of xylyleneglycol from the reaction mixture and recycling of the raw material and intermediate product to the reaction system. This separation process is not so easy and one pass conversion is low, so that the second method is also not an advantageous method industrially.

The present inventors studied the process for producing xylyleneglycol by reacting xylylenediamine with nitrite in the presence of mineral acid to solve the defects in the prior arts and to establish an industrially advantageous method.

It is well known that diazonium compound is formed by reacting primary amines with nitrite in the acidic solution and the reaction is called diazotization reaction. It is also well known that diazonium compound obtained by diazotization reaction of aliphatic primary amine is instable and decomposes to alcohol or olefine by water. However, the method for producing alcohol derivative by diazotization reaction of benzylamine or its derivatives, of which general formula is shown as

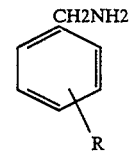

(wherein R is alkyl group)

and decomposing the resulting diazonium compound is not known except a few examples for the producing method of alcohol having special substituents, such as the producing method of p-diethylaminomethyl benzylalcohol from p-diethylaminomethyl benzylamine (Methoden der Organischen Chemie). Therefore the method for producing xylyleneglycol from xylylene diamine is not disclosed. When benzylamine derivative, especially xylylenediamine is diazotized and the resulting diazonium compound is decomposed to produce alcohol derivative, tarry material is easily formed and the yield of the objective alcohol derivative is low. For example, when the diazotization reaction of xylylenediamine is carried out by adding 2.5 to 3.0 mols of hydrochloric acid based on 1 mol of amino group (5.0 to 6.0 mols of hydrochloric acid based on 1 mol of xylylenediamine), most of the reaction product is tarry material and the yield of xylyleneglycol is limited to only 10 to 20%.

As described above, when benzylamine derivative is diazotized and the resulting diazonium salt is decomposed, tarry substance is easily formed. This is supposed to be the reason why benzylalcohol derivative had not been produced industrially by diazotization of benzylamine-type compound.

The present inventors studied the method for producing xylyleneglycol by the reaction of xylylenediamine with nitrite in the presence of mineral acid and decomposition of the resulting diazonium compound and found that the formation of tarry substance has a close relation with the quantity of the water in the reaction mixture and the PH of the reaction mixture, the formation of the tarry substance is suppressed and xylyleneglycol is produced with high yield by controlling the quantity of water and PH, and have established the present invention.

SUMMARY OF THE INVENTION

This invention relates to the process for producing xylyleneglycol which comprises reacting xylylenediamine with nitrite in the presence of more than 5 parts by weight of water per 1 part of the xylylenediamine, while maintaining the PH of the reaction mixture in the range of 1.5 to 5.0.

The xylylenediamine in the present invention is m-xylylenediamine, p-xylylenediamine and the mixture thereof. The xylyleneglycol in the present invention is m-xylyleneglycol, p-xylyleneglycol and the mixture thereof.

Nitrite includes inorganic nitrite, such as sodium nitrite, potassium nitrite, or barium nitrite etc. Mineral acid includes hydrochloric acid, sulfuric acid or phosphoric acid. Hydrochloric acid and sulfuric acid are preferable.

In the present invention, reaction can be carried out either as a semi-batch process or as a continuous process. A semi-batch process as an example is carried out as follows.

Specific amounts of xylylenediamine, water and mineral acid which are required to maintain the PH of the reaction mixture in the range of 1.5 to 5.0, preferably 2.5 to 4.5, are placed in the reaction vessel, the mixture is stirred at the temperature of 0° to 100° C., preferably 40° to 100° C. and sodium nitrite solution is added into the reaction mixture little by little. Diazotization reaction occures by adding sodium nitrite, the resulting diazonium compound decompose simultaneously and nitrogen gas is generated.

The reaction is carried out exothermically, while adding sodium nitrite at a specific rate into the reaction mixture and maintaining the reaction temperature in a specific range by controlling the heating degree or by cooling if required. The PH of the reaction mixture gradually becomes greater by adding sodium nitrite. When the PH exceeds 5, the reaction does not proceed smoothly. Therefore the PH of the reaction mixture should be maintained in the range of 1.5 to 5.0, preferably 2.5 to 4.5 by adding mineral acid according to the rise of the PH during the reaction.

After adding a specific amount of sodium nitrite, the reaction mixture is kept mixing at the reaction temperature until the nitrogen gas generation almost disappears.

The amount of water to be fed into the reactor is more than 5 parts, preferably 8 to 20 parts by weight per 1 part of the xylylenediamine to be reacted. If the amount of water is less than 5 parts by weight, the formation of condensation by-product is increased. If the amount of water is more than 20 parts by weight, there is no bad effect for the reaction, but volume efficiency is decreased and it is inefficient to treat the large amount of the reaction mixture.

The amount of mineral acid to be fed into the reactor at the beginning of the reaction is about 2.04 g-equivalent per 1 mol of xylylenediamine and is the amount which is required to maintain the PH of the reaction mixture in the range of 1.5 to 5.0, preferably 2.5 to 4.5.

When the reaction is carried out while adding sodium nitrite, PH of the reaction mixture increases gradually. It is more preferable, in order to suppress the formation of tarry substance and to increase the yield of xylyleneglycol, that mineral acid is added little by little into the reactor to maintain the PH in the range of 1.5 to 5.0, preferably 2.5 to 4.5, than that the whole amount of mineral acid is added into the reactor at once at the beginning of the reaction.

The diazotization reaction and decomposition of resulting diazonium compound is carried out at the temperature of 0° to 100° C., preferably 40° to 100° C., more preferably 70° to 100° C. When the reaction is carried out at the temperature of more than 40° C., especially 70° C., diazotization reaction and decomposition reaction concurrently occur, and not only the reaction is carried out at one stage, but the formation of tarry substance is suppressed. When the reaction temperature is below 70° C., especially 40° C., the decomposition rate of diazonium compound is slow, so that it is necessary to raise the temperature of the reaction mixture, after diazotization reaction was finished, to decompose the diazonium compound completely and convert it to xylyleneglycol.

The amount of nitrite to be used in the reaction is not restricted, but it is preferable to use the slightly excessive amount of nitrite to amino group of the xylylenediamine in order to carry out the reaction efficiently. In general, nitrite is used in an amount of 2.0 to 2.5 mols based on 1 mol of the xylylenediamine.

Mineral acid is added so as to maintain the PH of the reaction mixture in the range of 1.5 to 5.0, and in general, hydrochloric acid or sulfuric acid are added in an amount of 2.04 to 2.50, preferably 2.04 to 2.40 g-equivalent to xylylenediamine.

Reaction time (the time nitrite is added into the reaction system) is 20 minutes to 5 hours, preferably 30 minutes to 3 hours. Nitrite is added at the speed which the reaction temperature can be controlled and exhaustion of generated gas can be carried out properly according to the capacity of the reactor. After a specific amount of nitrite is added, reaction mixture is kept mixing for a while at the temperature of 70° to 100° C. until the generation of gas almost disappears. After the reaction is over, the reaction mixture is neutralized by alkaline substance and xylyleneglycol is separated and recovered according to the conventional method.

According to the present invention, high purity of xylyleneglycol can be easily obtained from xylylenediamine by the reaction under normal pressure in high yield.

PREFERRED EMBODIMENT OF THE INVENTION

EXAMPLE 1

600 g of water, 54.5 g (0.4 mols) of m-xylylenediamine and 81.1 g (0.80 mols) of 36 wt% hydrochloric acid solution were taken in a 1-l reactor equipped with stirrer, thermometer, PH meter, sodium nitrite solution supplier, dropping funnel of acid and cooler which is also used for gas outlet. After mixing, the resulting mixture was heated to 100° C. A small amount of 15 wt% hydrochloric acid was added from the dropping funnel under the control of PH meter, the PH of the mixture was adjusted to 2.5 and 152 g of 42 wt% sodium nitrite solution was gradually added to the mixture at the speed which every amount of the solution is added in about 2 hours.

Adding sodium nitrite solution, reaction occurs and heat and gas genaration can be observed. Reaction temperature was maintained at 100° C. by controlling heating and sodium nitrite solution was kept adding while agitating. As PH of the reaction mixture gradually rises as the reaction proceeds, 15 wt% hydrochloric acid solution was added to maintain the PH of the reaction mixture in the range of 2.5 to 4.5. 152 g of 42 wt% sodium nitrite solution was added in 2 hours. The amount of the 15 wt% hydrochloric acid solution used for maintaining the PH in the range of 2.5 to 4.5 was 19.5 g, which corresponds to 0.08 g-equivalent as HCL. The sum of hydrochloric acid used for the reaction was 0.88 g-equivalent as HCL.

After adding a specific amount of the sodium nitrite solution, the reaction mixture was agitated for 20 minutes at 100° C. and reaction was finished. Resulting reaction mixture amounted to 879 g and the concentration of m-xylyleneglycol was 5.73 wt%. This corresponds to 91.1 mol% of m-xylyleneglycol yield based on m-xylylenediamine charged.

After a small amount of caustic soda was added to the reaction mixture to neutralize the acid, a part of water in the reaction mixture was distilled off with rotary eveporator to obtain 297 g of concentrate. 300 g of methylisobutylketone were added to the concentrate and extraction was carried out. This procedure was repeated three times. The three extracts were mixed and methylisobutylketone was distilled off to obtain 52.9 g of residual liquid. The residual liquid was subjected to distillation under a reduced pressure of 3 mm Hg, and 46.9 g of the fraction which corresponds to m-xylyleneglycol was obtained. This corresponds to 84.8 mol% of m-xylyleneglycol yield based on the m-xylylenediamine charged and the purity was 99.4% through gas chromatograph analysis.

EXAMPLE 2

600 g of water, 54.5 g (0.4 mols) of p-xylylenediamine and 81.1 g (0.80 mols) of 36 wt% hydrochloric acid solution were taken into the same reactor with EXAMPLE 1 and the mixture was heated to 95° C. after mixing. A small amount of 15 wt% hydrochloric acid solution was added into the mixture in the same way as in EXAMPLE 1 to adjust the PH of the mixture to 2.5, 42 wt% of sodium nitrite solution was added gradually while controlling the PH in the range of 2.5 to 4.5 by adding hydrochloric acid and reaction was carried out at 95° C.

After adding 144.6 g of the sodium nitrite solution in 2 hours, the reaction mixture was agitated for 20 minutes at 95° C. and the reaction was finished. The total amount of 15 wt% hydrochloric acid solution used for maintaining the PH in the range of 2.5 to 4.5 during the reaction was 19.5 g (0.08 g-equivalent as HCL). The sum of hydrochloric acid used for the reaction was 0.88 g-equivalent as HCL.

The resulting reaction mixture amounted to 872 g and the concentration of p-xylyleneglycol was 5.84 wt% through gas chromatograph analysis. This corresponds to 92.1 mol% of p-xylyleneglycol yield based on p-xylylenediamine charged.

After a small amount of caustic soda solution was added to the reaction mixture to neutralize it, the reaction mixture was concentrated with rotary evaporator. Crystallization was occured on the way, the mixture was concentrated to 300 g and crystal was filtered out after cooling. 300 g of methylisobutylketone were added to the filtrate and the extraction was carried out. This procedure was repeated three times. The three extracts were mixed, the crystal filtered out before was added to the extract mixture, the crystal was melted by heating and the resulting mixture was subjected to distillation under the reduced pressure of 3 mm Hg. 47.6 g of the fraction which corresponds to p-xylyleneglycol was obtained. This corresponds to 86.1 mol% of p-xylyleneglycol yield based on the p-xylylenediamine charged. The purity of the product was 99.7% through gas chromatograph analysis.

EXAMPLE 3

650 g of water, 54.5 g (0.40 mols) of m-xylylenediamine and 40.9 g (0.40 mols) of 96 wt% sulfuric acid were taken into the same reactor with EXAMPLE 1 and the mixture was heated to 80° C. after mixing. After a small amount of 20 wt% sulfuric acid was added into the mixture to adjust the PH of the mixture to 2.5, 42 wt% sodium nitrite solution was added gradually into the mixture while controlling the PH in the range of 2.5 to 4.5 by adding sulfuric acid and reaction was carried out in the same way as in EXAMPLE 1, except that the reaction temperature was 80° C.

After adding 152 g of the sodium nitrite solution in 2 hours, the mixture was agitated for 30 minutes at 80° C. and the reaction was finished. The total amount of 20 wt% sulfuric acid used for maintaining the PH in the range of 2.5 to 4.5 during the reaction was 19.6 g and the sum of sulfuric acid used for the reaction was 0.88 g-equivalent.

The resulting reaction mixture was 887 g and the concentration of the m-xylyleneglycol in the reaction mixture was 5.56 wt% through gas chromatograph analysis. This corresponds to 89.2% of m-xylyleneglycol yield based on the m-xylylenediamine charged. The crude xylyleneglycol obtained from the reaction mixture in the same way as in EXAMPLE 1 was subjected to distillation under the reduced temperature of 3 mm Hg and 45.5 g of m-xylyleneglycol fraction was obtained. The yield of m-xylyleneglycol was 82.3 mol% based on the m-xylylenediamine charged and the purity was 99.2%.

EXAMPLE 4

600 g of water, 46.3 g (0.34 mols) of m-xylylenediamine and 68.9 g (0.68 mols) of 36 wt% hydrochloric acid were taken into the same reactor with EXAMPLE 1 and the mixture was heated to 100° C. while mixing. After a small amount of 15 wt% hydrochloric acid was added into the mixture to adjust the PH of the mixture to 2.5, 42 wt% sodium nitrite solution was gradually added into the mixture while maintaining the PH in the range of 2.5 to 4.5 by adding hydrochloric acid and the reaction was carried out at 100° C. in the same way as in EXAMPLE 1. After adding 140 g of the sodium nitrite solution in 2 hours, the reaction mixture was agitated for 30 minutes at 100° C. and the reaction was finished.

The total amount of hydrochloric acid used for maintaining the PH in the range of 2.5 to 4.5 during the reaction was 29.0 g and the sum of the hydrochloric acid used for the reaction was 0.80 g-equivalent.

The resulting reaction mixture was 859 g and the concentration of the m-xylyleneglycol in the reaction mixture was 5.10 wt% through gas chromatograph analysis. This corresponds to 93.2 mol% of m-xylyleneglycol yield based on the m-xylylenediamine charged. This reaction mixture was treated in the same way as in EXAMPLE 1 and subjected to distillation under the reduced pressure of 3 mm Hg and 41.6 g of m-xylyleneglycol fraction was obtained. This corresponds to 88.5 mol% of m-xylyleneglycol yield based on the m-xylylenediamine charged. The purity of the product was 98.9% through gas chromatograph analysis.

COMPARATIVE EXAMPLE 1 (PH was not controlled and the quantity of water was less than 5 parts)

240 g of water, 112 g of 36 wt% hydrochloric acid solution and 68.1 g (0.50 mols) of m-xylylenediamine were taken into the same reactor with EXAMPLE 1 and the mixture was heated to 100° C. Maintaining 100° C., 42 wt% sodium nitrite solution was added to the mixture while agitating and the reaction was carried out. After adding 189 g of the sodium nitrite solution in 2 hours, the mixture was agitated for 20 minutes at 100° C. and the reaction was finished.

The resulting reaction mixture was 577 g and the concentration of the m-xylyleneglycol in the reaction mixture was 7.30 wt% through gas chromatograph analysis. This corresponds to 61.0 mol% of m-xylyleneglycol yield based on the m-xylylenediamine charged. After cooling the reaction mixture, a large amount of brown oily substance was perceived. After neutralizing, the reaction mixture was concentrated to 370 g with rotarry evaporator, extraction was carried out in the same way as in Example 1 and 64.9 g of oily substance was obtained. This substance was subjected to distillation under the reduced pressure of 3 mm Hg and 36.7 g of the fraction which corresponds to m-xylyleneglycol were obtained.

The distillation residue was 28.2 g of blackish brown tarry substance. The yield of the m-xylyleneglycol was 53.1 mol% based on the m-xylylenediamine charged.

COMPARATIVE EXAMPLE 2 (PH was controlled, but the quantity of water was less than 5 parts)

The reaction was conducted while maintaining the PH of the reaction mixture in the range of 2.5 to 4.5 in the same way as in EXAMPLE 1, except that 193 g of water was charged instead of 600 g of water.

The resulting reaction mixture was 472 g and the concentration of the m-xylyleneglycol in the reaction mixture was 7.98 wt% through gas chromatograph analysis. This corresponds to 68.1 mol% of m-xylyleneglycol yield based on the m-xylylenediamine charged. After cooling the reaction mixture, a large amount of oily substance was perceived.

COMPARATIVE EXAMPLE 3 (PH was not controlled)

The reaction was conducted in the same way as in EXAMPLE 1, except that 19.5 g of 15 wt% hydrochloric acid was charged before the commencement of the reaction and the PH was not controlled during the reaction.

The resulting reaction mixture was 881 g and the concentration of the m-xylyleneglycol in the reaction mixture was 4.94 wt% through gas chromatograph analysis. This corresponds to 78.7 mol% of m-xylyleneglycol yield based on the m-xylylenediamine charged.

What is claimed is:

1. A process for producing xylyleneglycol, which comprises reacting xylylenediamine with nitrite at 0° to 100° C. in the presence of more than 5 parts by weight of water per 1 part of the xylylenediamine, while maintaining the PH of the reaction mixture in the range of 1.5 to 5.0.

2. The process according to claim 1, wherein the PH is maintained by adding mineral acid into the reaction mixture.

3. The process according to claim 2, wherein the mineral acid is hydrochloric acid, sulfuric acid or phosphoric acid.

4. The process according to claim 1, wherein the nitrite is sodium nitrite, potassium nitrite or barium nitrite.

5. The process according to claim 1, wherein the reaction is carried out while adding 2.04 to 2.50 g-equivalent of hydrochloric acid or sulfuric acid based on the xylylenediamine.

6. A process for producing xylyleneglycol, which comprises reacting xylylenediamine with nitrite by carrying out a diazotization reaction at 0° to 40° C. in the presence of more than 5 parts by weight of water per 1 part of the xylylenediamine, while maintaining the pH of the reaction mixture in the range of 1.5 to 5.0 and decomposing the resulting diazonium compound at 40° to 100° C.

7. The process according to claim 6, wherein the pH is maintained by adding mineral acid into the reaction mixture.

8. The process according to claim 7, wherein the mineral acid is hydrochloric acid, sulfuric acid or phosphoric acid.

9. The process according to claim 6, wherein the nitrite is sodium nitrite, potassium nitrite or barium nitrite.

10. The process according to claim 6, wherein the reaction is carried out, while adding 2.04 to 2.50 g-equivalent of hydrochloric acid or sulfuric acid based on the xylylenediamine.

11. A process for producing xylyleneglycol, which comprises reacting xylylenediamine with nitrite by carrying out a diazotization reaction and decomposition of the resulting diazonium compound simultaneously at 40° to 100° C. in the presence of more than 5 parts by weight of water per 1 part of the xylylenediamine, while maintaining the pH of the reaction mixture in the range of 1.5 to 5.0.

12. The process according to claim 11, wherein the pH is maintained by adding mineral acid into the reaction mixture.

13. The process according to claim 12, wherein the mineral acid is hydrochloric acid, sulfuric acid or phosphoric acid.

14. The process according to claim 11, wherein the nitrite is sodium nitrite, potassium nitrite or barium nitrite.

15. The process according to claim 11, wherein the reaction is carried out, while adding 2.04 to 2.50 g-equivalent of hydrochloric acid or sulfuric acid based on the xylylenediamine.

* * * * *